United States Patent
Rafaelides et al.

[11] Patent Number: 5,334,361
[45] Date of Patent: Aug. 2, 1994

[54] CAR AIR FRESHENER

[76] Inventors: Anthony Rafaelides, 77-15 Ditmars Blvd. #2-B, Jackson Heights, N.Y. 11370; George Spector, 233 Broadway Rm 702, New York, N.Y. 10279

[21] Appl. No.: 35,173
[22] Filed: Mar. 22, 1993
[51] Int. Cl.$^5$ .............................. A61L 9/00
[52] U.S. Cl. ................... 422/305; 239/34; 239/211; 422/5
[58] Field of Search ............ 422/305, 15; 239/34, 239/53, 56, 57, 211

[56] References Cited

U.S. PATENT DOCUMENTS

| Re. 32,513 | 10/1987 | Seaber et al. | 239/34 |
|---|---|---|---|
| 2,209,914 | 7/1940 | Gerber et al. | 239/34 |
| 2,303,073 | 11/1942 | Brown | 239/53 |
| 2,757,957 | 8/1956 | Samann | 239/53 |
| 4,158,440 | 6/1979 | Sullivan et al. | 239/56 |
| 4,283,011 | 8/1981 | Spector | 239/56 |
| 4,345,716 | 8/1982 | Armstrong et al. | 239/56 |
| 4,419,395 | 12/1983 | Sugimoto | 239/56 |
| 4,529,125 | 7/1985 | Sullivan | 239/56 |
| 4,534,509 | 8/1985 | Holzner | 239/34 |
| 4,535,935 | 8/1985 | Spector | 239/211 |
| 4,874,129 | 10/1989 | DiSapio et al. | 239/53 |
| 4,990,381 | 2/1991 | Holzner | 239/34 |

FOREIGN PATENT DOCUMENTS

| 1056657 | 3/1986 | Japan | 239/53 |
|---|---|---|---|
| 0200580 | 9/1991 | Japan | 239/34 |

*Primary Examiner*—James C. Housel
*Assistant Examiner*—Laura E. Collins

[57] ABSTRACT

An air freshener is provided which consists of a housing made of a porous material in the form and appearance of a bottle of fragrance, which can be hung from a cord, so that the fragrance can be release from a scent pad carried in a pocket of the housing. In a modification a squeeze bulb can be built into the housing, so as to help release the fragrance from the scent pad when the squeeze bulb is depressed.

2 Claims, 1 Drawing Sheet

CAR AIR FRESHENER

BACKGROUND OF THE INVENTION

The instant invention relates generally to aromatic articles and more specifically it relates to an air freshener which provides a bottle shaped housing that will release a matching fragrance from a scent pad.

There are available various conventional aromatic articles which do not provide the novel improvements of the invention herein disclosed.

SUMMARY OF THE INVENTION

A primary object of the present invention is to provide an air freshener that will overcome the shortcomings of the prior art devices.

Another object is to provide an air freshener in which its housing made of porous material is in the form and appearance of a bottle of fragrance which can be hung from a cord, so that the fragrance can be released from a scent pad carried in a pocket of the housing.

An additional object is to provide an air freshener that contains a squeeze bulb built therein so as to help release the fragrance from the scent pad.

A further object is to provide an air freshener that is simple and easy to use.

A still further object is to provide an air freshener that is economical in cost to manufacture.

Further objects of the invention will appear as the description proceeds.

To the accomplishment of the above and related objects, this invention may be embodied in the form illustrated in the accompanying drawings, attention being called to the fact, however, that the drawings are illustrative only, and that changes may be made in the specific construction illustrated and described within the scope of the appended claims.

BRIEF DESCRIPTION OF THE DRAWING FIGURES

DETAILED DESCRIPTION OF THE PREFERRED EMBODIMENTS

Figure 1:
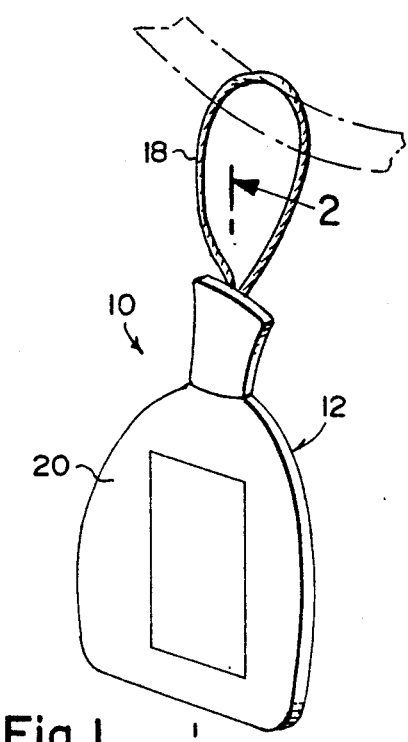
FIG. 1 is a perspective view of a first embodiment of the instant invention.
Figure 2:
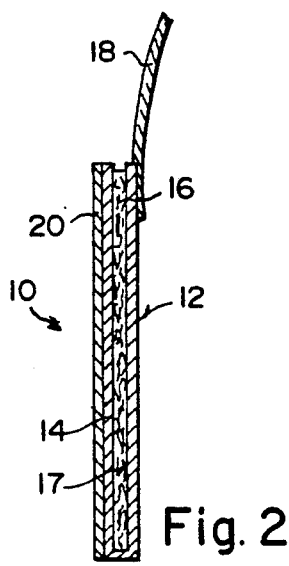
FIG. 2 is a cross sectional view taken along line 2—2 in FIG. 1, showing a housing made of porous material, having a pocket with a porous picture of a bottle on a front surface and a scent pad inserted within the pocket.

Turning now descriptively to the drawings, in which similar reference characters denote similar elements throughout the several views, the Figures illustrate an air freshener 10 which consists of a housing 12 made of a porous material and having a pocket 14. A scent pad 16 impregnated with a fragrance 17 is inserted within the pocket 14. A cord 18 is attached to the housing 12, so that the housing 12 can be suspended to allow the scent pad 16 to release the fragrance 17 into the air and give the air a pleasant odor.

The housing 12 is shaped as a fragrance bottle. A porous picture 20 of the fragrance bottle is applied to a front surface of the housing 12. The fragrance 17 matches up with the fragrance bottle picture 20, so that when the housing 12 is suspended by the cord 18, the fragrance bottle will be simulated therefrom.

Figure 3:
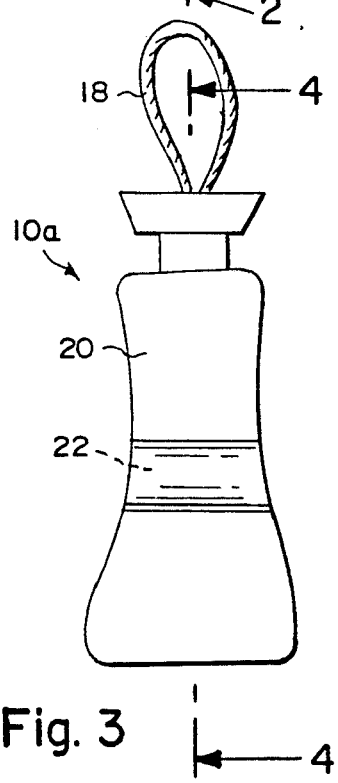
FIG. 3 is a front view of a second embodiment of the instant invention.
Figure 4:
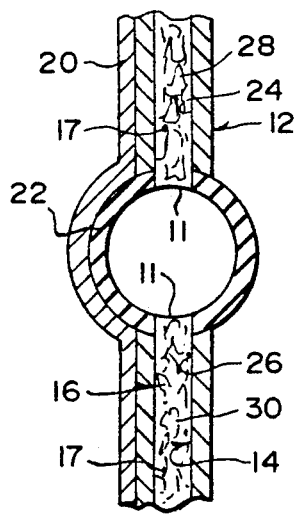
FIG. 4 is an enlarged cross sectional view taken along line 4—4 in FIG. 3, showing the rubber squeeze bulb in greater detail.

A modified air freshener 10a, shown in FIGS. 3 and 4, includes a flexible squeeze bulb 22, including a pair of openings 11, built into the housing 12 to divide the pocket 14 into two chambers 24 and 26. The scent pad 16 is divided into two parts 28 and 30 on opposite sides of the flexible squeeze bulb 22, within the two chambers 24 and 26 of the pocket 14. A manual depression of the flexible squeeze bulb 22 will help release the fragrance 17 from the two parts 28 and 30 of the scent pad 16.

Figure 5:
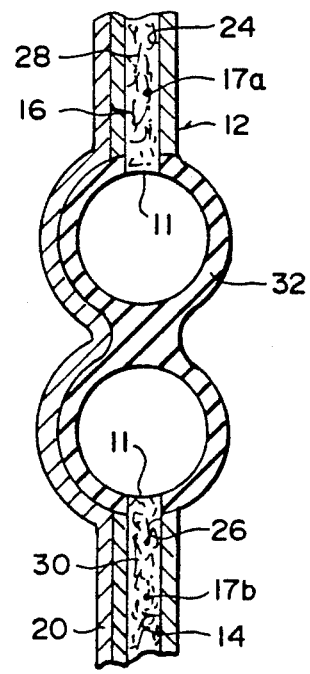
FIG. 5 is an enlarged cross sectional view similar to FIG. 4, showing a double rubber squeeze bulb for two different scent pads therein.

FIG. 5 shows an additional modification, in which a double flexible squeeze bulb 32 is built into the housing 12, to divide the pocket 14 into two chambers 24 and 26. The scent pad 16 is divided into two parts 28 and 30 on opposite sides of the double flexible squeeze bulb 32 within the two chambers 24 and 26 of the pocket 14. Each part 28 and 30 of the scent pad 16 is impregnated with a different fragrance 17a and 17b. A manual depression of either portion of the double squeeze bulb 32 will help release the respective fragrance 17a, 17b from the respective part 28, 30 of the scent pad 16.

While certain novel features of this invention have been shown and described and are pointed out in the annexed claims, it will be understood that various omissions, substitutions and changes in the forms and details of the device illustrated and in its operation can be made by those skilled in the art without departing from the spirit of the invention.

What is claimed is:

1. An air freshener which comprises:
   a) a housing made of a porous material and having a pocket;
   b) a scent pad impregnated with a fragrance inserted within said pocket;
   c) a cord attached to said housing so that said housing can be suspended to allow said scent pad to release said fragrance into air and give the air a pleasant odor; and
   d) a flexible squeeze bulb having a pair of openings and provided in said housing to divide said pocket into two separated chambers each opening communicating with a respective one of said chambers; and
   e) said scent pad being divided into two separated parts on opposite sides of and in communication with said flexible squeeze bulb within said two chambers of said pocket so that a manual depression of said flexible squeeze bulb will help release said fragrance from said two parts of said scent pad.

2. An air freshener as recited in claim 1, wherein said bulb comprises:
   a double flexible squeeze bulb with two separate compartments, each compartment having one of said openings, and p1 said parts of said scent pad being disposed on respective opposite sides of said double flexible squeeze bulb within said two chambers of said pocket, each said part of said scent pad impregnated with a different fragrance and in communication with one of said compartments so that a manual depression of either compartment of said double squeeze bulb will help release one respective fragrance from said respective part of said scent pad in communication with the compartment squeezed.

* * * * *